(12) United States Patent
Nishio

(10) Patent No.: US 11,717,313 B2
(45) Date of Patent: Aug. 8, 2023

(54) MEDICAL DEVICE

(71) Applicant: TERUMO KABUSHIKI KAISHA, Tokyo (JP)

(72) Inventor: Kousuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1137 days.

(21) Appl. No.: 16/351,640

(22) Filed: Mar. 13, 2019

(65) Prior Publication Data
US 2019/0201050 A1 Jul. 4, 2019

Related U.S. Application Data

(63) Continuation of application No. PCT/JP2017/033487, filed on Sep. 15, 2017.

(30) Foreign Application Priority Data

Sep. 16, 2016 (JP) .................................. 2016-182404

(51) Int. Cl.
*A61B 17/3207* (2006.01)
*A61B 17/32* (2006.01)
(Continued)

(52) U.S. Cl.
CPC .. *A61B 17/320725* (2013.01); *A61B 17/1659* (2013.01); *A61B 17/32002* (2013.01);
(Continued)

(58) Field of Classification Search
CPC ........ A61B 17/3207; A61B 17/320758; A61B 17/32002; A61B 17/320725; A61B 17/32075; A61B 17/1659
See application file for complete search history.

(56) References Cited

U.S. PATENT DOCUMENTS 4,664,112 A 5/1987 Kensey et al.
4,679,558 A 7/1987 Kensey et al.
(Continued)

FOREIGN PATENT DOCUMENTS

CN 101795630 A 8/2010
CN 103142308 A 6/2013
(Continued)

OTHER PUBLICATIONS

Office Action (Notice of Reasons for Refusal) dated Apr. 27, 2021, by the Japanese Patent Office in corresponding Japanese Patent Application No. 2018-539188 and an English Translation of the Office Action (9 pages).
(Continued)

*Primary Examiner* — Diane D Yabut
(74) *Attorney, Agent, or Firm* — Buchanan Ingersoll & Rooney PC

(57) ABSTRACT

A medical device for cutting an object S in a body lumen is disclosed, which includes: a rotatable drive shaft; a tubular outer sheath configured to accommodate the drive shaft in a rotatable manner; a rotation structure, the rotation structure comprising an accommodation portion configured to be disposed inside the outer sheath; an exposed portion, the exposed portion being located at a distal side of the accommodation portion and is provided with a cutting portion, in which the accommodation portion is provided to be rotatable by the drive shaft, and a side surface of the accommodation portion and a side surface of the exposed portion have a groove portion, the groove portion extending from the accommodation portion to the exposed portion.

21 Claims, 8 Drawing Sheets

(51) Int. Cl.
  *A61B 17/16* (2006.01)
  *A61B 17/00* (2006.01)

(52) U.S. Cl.
  CPC .............. *A61B 17/320758* (2013.01); *A61B 17/32075* (2013.01); *A61B 2017/00845* (2013.01); *A61B 2217/005* (2013.01)

(56) References Cited

U.S. PATENT DOCUMENTS

| | | | |
|---|---|---|---|
| 4,681,106 A | | 7/1987 | Kensey et al. |
| 4,700,705 A | | 10/1987 | Kensey et al. |
| 4,747,821 A | | 5/1988 | Kensey et al. |
| 5,376,100 A | * | 12/1994 | Lefebvre ........ A61B 17/320725 606/180 |
| 6,565,588 B1 | | 5/2003 | Clement et al. |
| 2008/0045986 A1 | | 2/2008 | To et al. |
| 2008/0103439 A1 | | 5/2008 | Torrance et al. |
| 2008/0103446 A1 | | 5/2008 | Torrance et al. |
| 2008/0103516 A1 | | 5/2008 | Wulfman et al. |
| 2011/0118660 A1 | * | 5/2011 | Torrance ........ A61B 17/320758 604/35 |
| 2012/0109171 A1 | * | 5/2012 | Zeroni ........... A61B 17/320758 606/159 |
| 2014/0031844 A1 | | 1/2014 | Kusleika |
| 2015/0150590 A1 | | 6/2015 | Zeroni et al. |
| 2016/0287284 A1 | * | 10/2016 | Smith ............ A61B 17/320725 |
| 2017/0367719 A1 | | 12/2017 | Matsushita et al. |

FOREIGN PATENT DOCUMENTS

| | | |
|---|---|---|
| CN | 103200886 A | 7/2013 |
| CN | 104382632 A | 3/2015 |
| JP | 2500568 A | 3/1990 |
| JP | 2010505542 A | 2/2010 |
| JP | 2010532211 A | 10/2010 |
| JP | 2014501552 A | 1/2014 |
| WO | 2016/132241 A1 | 8/2016 |
| WO | 2016/143846 A1 | 9/2016 |

OTHER PUBLICATIONS

Office Action (Notification of the First Office Action) dated Dec. 1, 2020, by the National Intellectual Property Administration, PRC in corresponding Chinese Patent Application No. 201780057014.9 and an English Translation of the Office Action. (15 pages).

International Search Report (PCT/ISA/210) dated Nov. 21, 2017, by the Japanese Patent Office as the International Searching Authority for International Application No. PCT/JP2017/033487.

Written Opinion (PCT/ISA/237) dated Nov. 21, 2017, by the Japanese Patent Office as the International Searching Authority for International Application No. PCT/JP2017/033487.

\* cited by examiner

MEDICAL DEVICE

CROSS-REFERENCES TO RELATED APPLICATIONS

This application is a continuation of International Application No. PCT/JP2017/033487 filed on Sep. 15, 2017, which claims priority to Japanese Application No. 2016-182404 filed on Sep. 16, 2016, the entire content of both of which is incorporated herein by reference.

FIELD OF THE INVENTION

The present disclosure generally relates to a medical device.

BACKGROUND DISCUSSION

As a treatment for a body lumen (intravascular) against arteriosclerosis, atherectomy, which cuts a stenotic object (object) formed by thrombus, plaque, calcified lesion, and the like is known. Atherectomy is an important treatment for improving arterial patency after treatment. As the atherectomy, a method of cutting and removing a stenotic object by bringing a rotation body into contact with the stenotic body is mainly adopted nowadays. As such an atherectomy device, a device which includes a drive shaft accommodated in an outer sheath to be rotatable and a rotation structure connected to the drive shaft and cuts a stenotic object by a cutting portion (blade) provided in the rotation structure rotated through the drive shaft (for example, see U.S. Pat. No. 6,565,588).

There is a desire to efficiently cut a stenotic object in a body lumen in a relatively short time. However, when the stenotic object cutting efficiency is improved by increasing the rotation speed of the rotation structure, there is a concern that a biological tissue such as a blood vessel may be damaged with an increase in temperature due to heat generated by friction between the stenotic object and the cutting portion of the rotating rotation structure.

SUMMARY

A medical device is disclosed, which is capable of reducing the risk of damaging a biological tissue with an increase in temperature.

In accordance with an exemplary embodiment, a medical device is disclosed for cutting an object in a body lumen, which includes: a rotatable drive shaft; a tubular outer sheath which accommodates the drive shaft in a rotatable manner; an accommodation portion which is disposed inside the outer sheath; and an exposed portion which is located at a distal side of the accommodation portion and is provided with a cutting portion, in which the accommodation portion is provided to be rotatable by the drive shaft, and a side surface of the accommodation portion and a side surface of the exposed portion have a groove portion which extends from the accommodation portion to the exposed portion.

In the medical device of the present disclosure, the side surface of the accommodation portion preferably has a plurality of rolling element holding spaces formed at intervals in a circumferential direction and each holding a rolling element, and the groove portion is preferably disposed between the plurality of rolling element holding spaces.

Further, in the medical device of the present disclosure, an edge of the groove portion preferably forms the cutting portion.

Further, in the medical device of the present disclosure, the groove portion preferably forms a liquid supply channel for supplying a cooling liquid to the exposed portion.

Further, in the medical device of the present disclosure, the groove portion preferably forms a suction channel for sucking a cut object.

In accordance with an aspect, a medical device is disclosed for cutting an object in a body lumen, comprising: a rotatable drive shaft; a tubular outer sheath configured to accommodate the drive shaft in a rotatable manner; and a rotation structure, the rotation structure comprising: an accommodation portion configured to be disposed inside the outer sheath; an exposed portion, the exposed portion being located at a distal side of the accommodation portion and is provided with a cutting portion, the accommodation portion being configured to be rotatable by the drive shaft; and a side surface of the accommodation portion and a side surface of the exposed portion have a groove portion, the groove portion extending from the accommodation portion to the exposed portion.

In accordance with another aspect, a medical device for cutting an object in a body lumen, comprising: a rotatable drive shaft; a tubular outer sheath configured to accommodate the drive shaft in a rotatable manner; a rotation structure comprising: an accommodation portion configured to be disposed inside the outer sheath; an exposed portion, the exposed portion being located at a distal side of the accommodation portion and is provided with a cutting portion, the accommodation portion being configured to be rotatable by the drive shaft; and a side surface of the accommodation portion and a side surface of the exposed portion have a groove portion, the groove portion extending from the accommodation portion to the exposed portion; and an annular bearing member configured to be provided between the outer sheath and the accommodation portion of the rotation structure.

In accordance with a further aspect, a method is disclosed for cutting substances inside a body lumen using a medical device including a rotatable drive shaft, a tubular outer sheath configured to accommodate the drive shaft in a rotatable manner, and a rotatable rotation structure, the rotation structure comprising an accommodation portion configured to be disposed inside the outer sheath, an exposed portion, the exposed portion being located at a distal side of the accommodation portion and is provided with a cutting portion, the accommodation portion being configured to be rotatable by the drive shaft, and a side surface of the accommodation portion and a side surface of the exposed portion have a groove portion, the groove portion extending from the accommodation portion to the exposed portion, the method comprising: inserting the rotatable rotation structure into the body lumen; moving the rotatable rotation structure in a distal direction; rotating the rotatable rotation structure with the rotatable drive shaft; and cutting the substances inside the body lumen with the rotatable rotation structure during the movement of the rotatable rotation structure in the distal direction.

According to the medical device of the present disclosure, the risk of damaging a biological tissue with an increase in temperature can be reduced.

BRIEF DESCRIPTION OF DRAWINGS

FIG. 5A illustrates a state in which a stenotic part is cut while the medical device is press-inserted and FIG. 5B illustrates a state in which the stenotic part is cut while the medical device is pulled.

DESCRIPTION OF EMBODIMENTS

Figure 1:
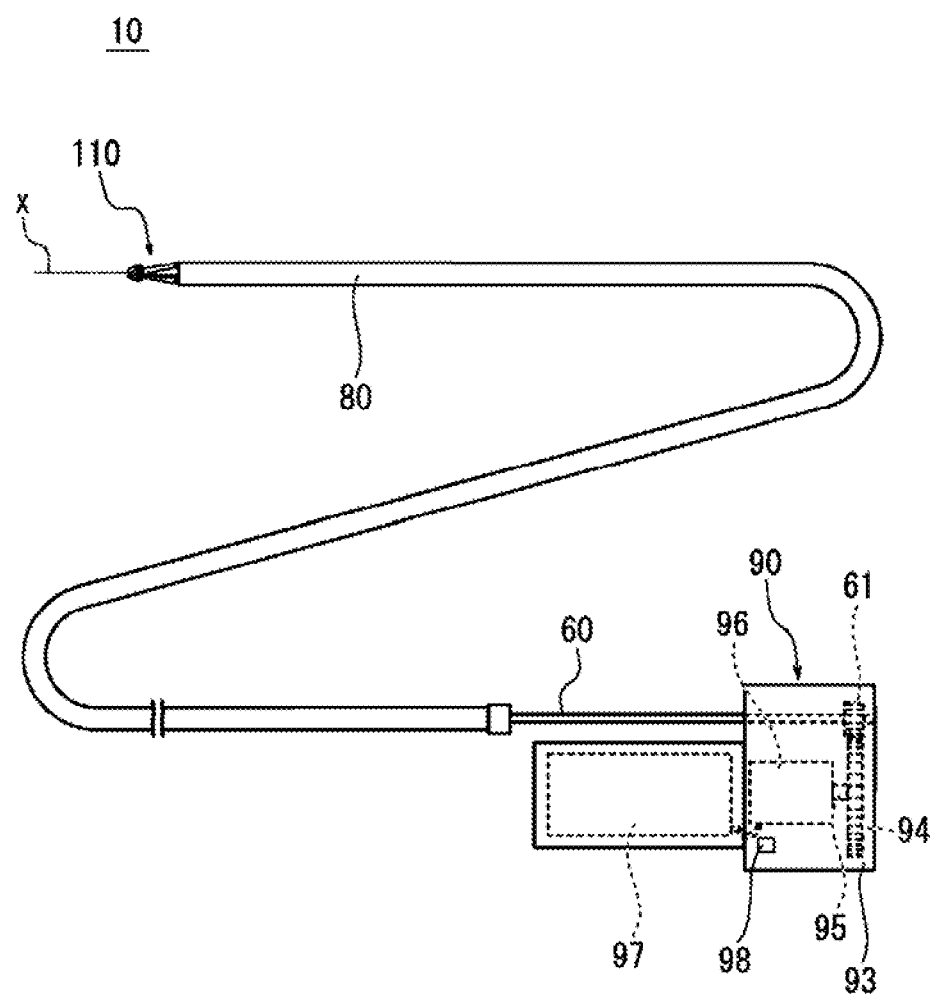
FIG. 1 is a diagram illustrating a medical device according to an embodiment of the present disclosure.

Hereinafter, an embodiment of the present disclosure will be described with reference to the drawings. Dimension ratios in the drawings may be exaggerated and may differ from actual ratios for convenience of description. Further, in each drawing, common members are denoted by the same reference numerals. Further, in this specification, the side to be inserted into the blood vessel of the medical device will be referred to as the "distal side" and the side to be operated will be referred to as the "proximal side".

Figure 2:
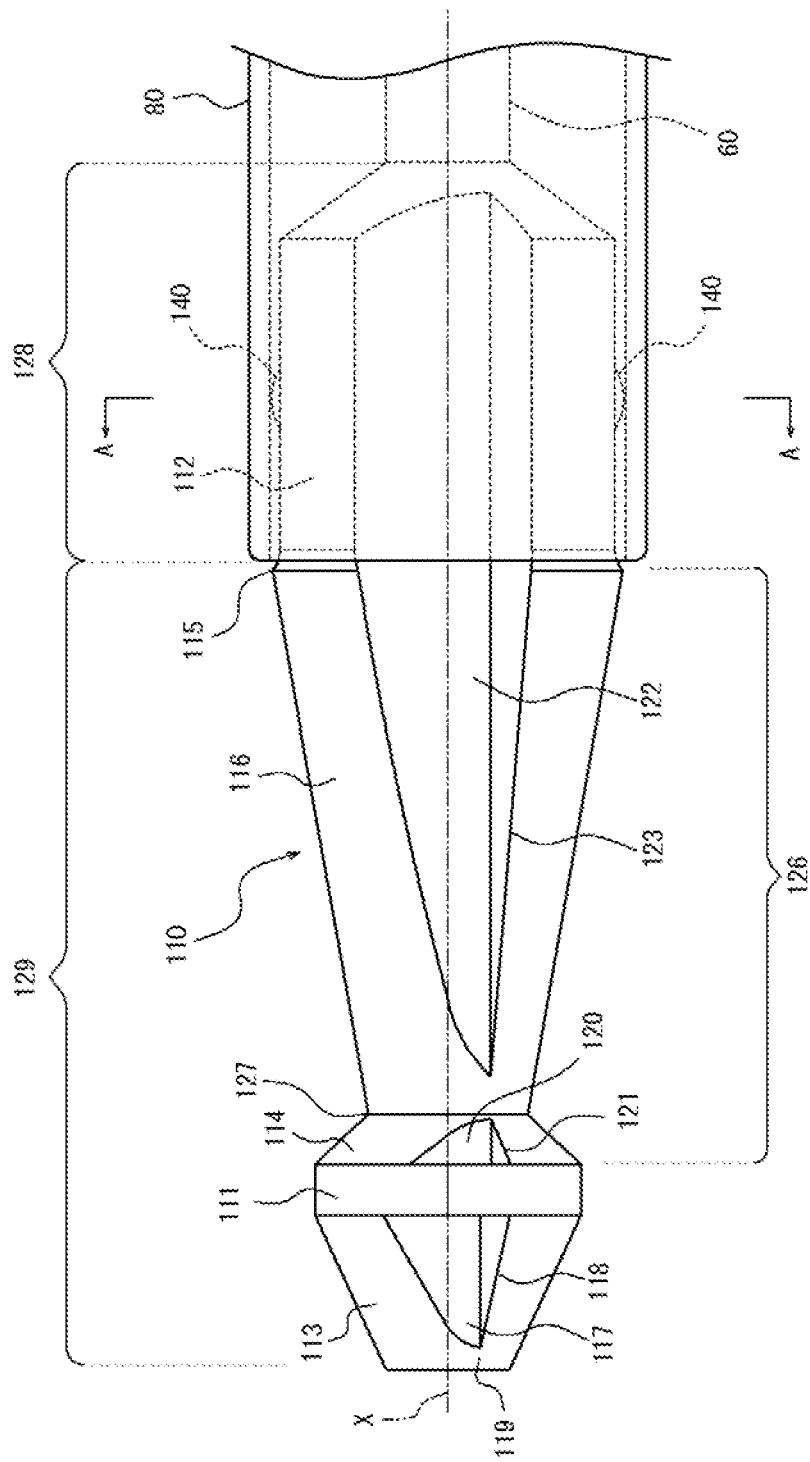
FIG. 2 is an enlarged plan view of a distal side of the medical device illustrated in FIG. 1.
Figure 3:
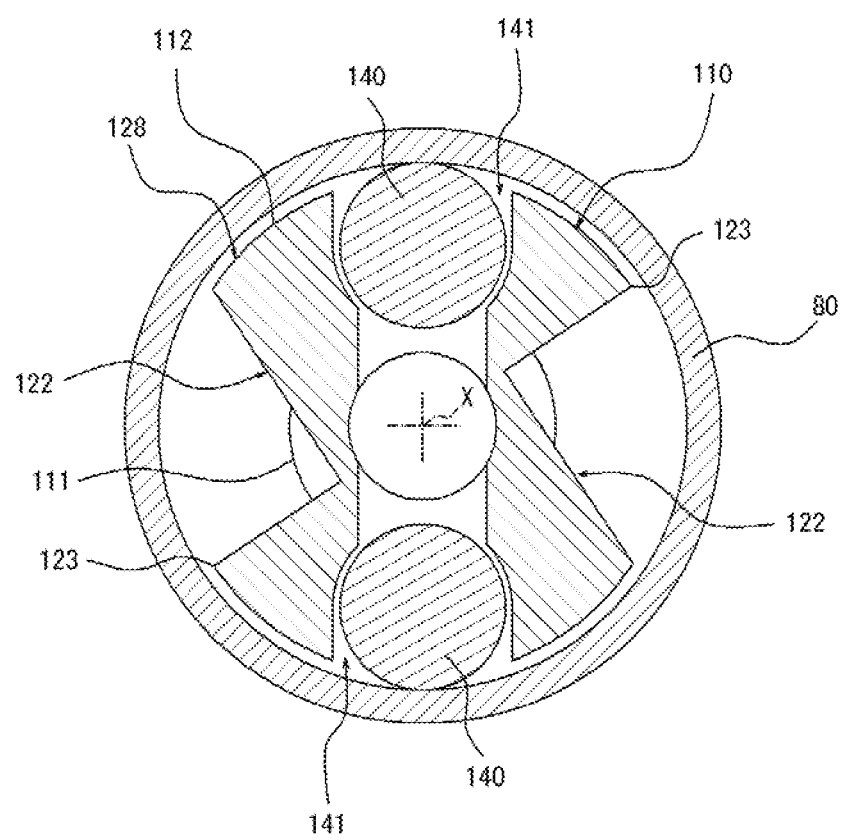
FIG. 3 is a cross-sectional view taken along a line A-A of the medical device illustrated in FIG. 2.
Figure 4:
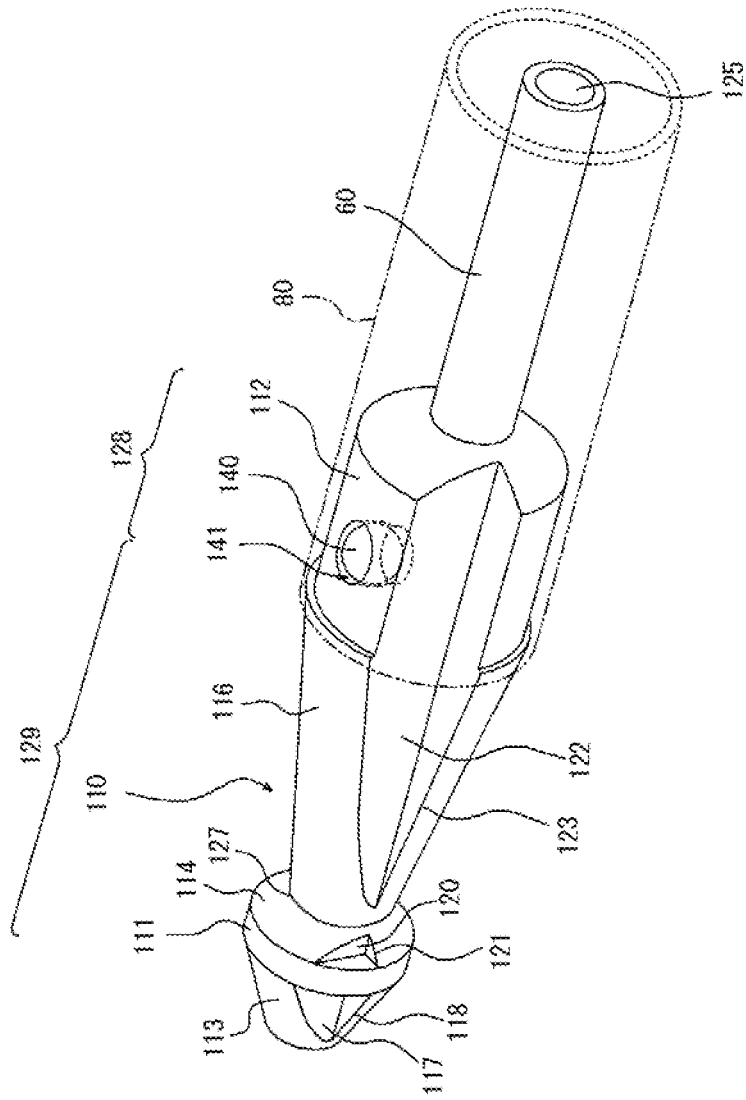
FIG. 4 is an enlarged perspective view of a distal side of the medical device illustrated in FIG. 1.

First, a configuration of a medical device 10 according to an embodiment of the present disclosure will be described with reference to FIGS. 1 to 4. FIG. 1 is a diagram illustrating a medical device 10 according to an embodiment of the present disclosure. FIG. 2 is an enlarged plan view of the distal side of the medical device 10 illustrated in FIG. 1. FIG. 3 is a cross-sectional view taken along the line A-A of the medical device 10 illustrated in FIG. 2. FIG. 4 is an enlarged perspective view of the distal side of the medical device 10 illustrated in FIG. 1.

The medical device 10 is used in a treatment of cutting an object inside a body lumen, for example, a treatment of cutting a stenotic object S (see FIGS. 5A and 5B) caused by plaque, calcified lesions, and thrombus inside a blood vessel. Next, a case of cutting a stenotic object S inside a blood vessel will be described as a detailed example.

In accordance with an exemplary embodiment, the medical device 10 can include, as illustrated in FIG. 1, a rotation structure 110 which is rotatable along a rotation axis X and is able to cut a stenotic object S, a drive shaft 60 which drives the rotation of the rotation structure 110, a tubular outer sheath 80 which is able to accommodate the drive shaft 60, and an operation unit 90 which operates the rotation structure 110 and the drive shaft 60.

As illustrated in FIG. 2, the rotation structure 110 is connected to the drive shaft 60 and is driven by the drive shaft 60 when the drive shaft 60 rotates so that the rotation structure 110 rotates. The rotation of the drive shaft 60 is controlled by the operation unit 90 illustrated in FIG. 1. A detailed structure of the rotation structure 110 will be described later.

In accordance with an exemplary embodiment, the drive shaft 60 is formed in a tubular shape. As illustrated in FIG. 1, the distal side of the drive shaft 60 is fixed to the rotation structure 110 and the proximal side of the drive shaft 60 is fixed to the driven gear 61 inside the operation unit 90.

In accordance with an exemplary embodiment, the drive shaft 60 is flexible and has a characteristic in which a rotational force exerted at the proximal side is transmitted to the distal side. The drive shaft 60 has, for example, a configuration in which a reinforcement member such as a wire formed of polyolefin such as polyethylene and polypropylene, polyamide, polyester such as polyethylene terephthalate, fluorine-based polymer such as ETFE, polyetheretherketone (PEEK), polyimide, or a combination of polyolefin, polyamide, polyester, fluorine-based polymer, polyetheretherketone (PEEK), and/or polyimide is buried in a multi-layer coiled tubular body such as a three-layered coil wound alternately at the right and left sides in the winding direction.

The inner diameter of the drive shaft 60 can be appropriately selected, for example, the inner diameter of the drive shaft 60 can be 0.4 mm to 1.6 mm and can be set to 0.7 mm as an example. The outer diameter of the drive shaft 60 can be appropriately selected, for example, the outer diameter of the drive shaft 60 can be 0.6 mm to 1.6 mm and can be set to 1.0 mm as an example.

A guide wire lumen 125 (see FIG. 4) into which a guide wire 130 (see FIGS. 5A and 5B) is insertable is provided inside the drive shaft 60. The guide wire 130 is used to guide the rotation structure 110 when advancing the rotation structure 110 inside a blood vessel.

In accordance with an exemplary embodiment, the outer sheath 80 is a tubular body which accommodates the drive shaft 60 in a rotatable manner and is movable and rotatable in a direction (axial direction) along the rotation axis X with respect to the drive shaft 60. The outer sheath 80 can be operated while the proximal portion is gripped, can accommodate the rotation structure 110 in the outer sheath 80 while being moved to the distal side, and can expose a part of the rotation structure 110 to the outside while being moved to the proximal side. Further, the inner diameter of the outer sheath 80 is smaller than a maximum diameter of a first tapered portion 116. For that reason, since it is possible to further transmit a force in which the rotation structure 110 presses the intravascular wall by the outer sheath 80, a cutting operation can be effectively performed.

The material of forming the outer sheath 80 is not particularly limited, for example, the material of the outer sheath can be polyolefins such as polyethylene and polypropylene, polyamides, polyesters such as polyethylene terephthalate, fluorine polymers such as PTFE, polyetheretherketone (PEEK), polyimide, and the like. Further, the outer sheath 80 may be formed of a plurality of materials or a reinforcement member such as a wire may be buried in the material or the plurality of materials of the outer sheath 80.

The inner diameter of the outer sheath 80 can be appropriately selected, for example, the inner diameter of the outer sheath 80 can be 1.2 mm to 2.5 mm and can be set to 1.8 mm as an example. The outer diameter of the outer sheath 80 can be appropriately selected, for example, the outer diameter of the outer sheath 80 can be 1.3 mm to 2.6 mm and can be set to 2.0 mm as an example.

In accordance with an exemplary embodiment, the operation unit 90 includes, as illustrated in FIG. 1, a drive mechanism 93 which applies a rotational force to the drive shaft 60. The drive mechanism 93 can include a drive gear 94 which meshes with the driven gear 61, a motor 96 which is a drive source including a rotation axis 95 to which the drive gear 94 is fixed, a battery 97, for example, a battery or the like, which is configured to supply electric power to the motor 96, and a switch 98, which controls the driving of the motor 96. When the rotation axis 95 of the motor 96 is rotated by turning on the switch 98, the driven gear 61 meshing with the drive gear 94 rotates and the drive shaft 60 rotates. When the drive shaft 60 rotates, the rotation structure 110 fixed to the distal side of the drive shaft 60 rotates. The mechanism of the operation unit 90 is not limited to the operation mechanism as described above, and a variety of operation mechanisms capable of controlling the rotation of the drive shaft 60 may be used.

Subsequently, a structure of the rotation structure 110 will be described. In the description below, the "distal side" means the distal side of the rotation structure 110 and the "proximal side" means the proximal side of the rotation structure 110.

As illustrated in FIG. 2, the rotation structure 110 includes a proximal side accommodation portion 128, which is disposed inside the outer sheath 80 when cutting an object such as a stenotic object S in a body lumen and an exposed portion 129, which is located at the distal side of the accommodation portion 128 and is provided with a first cutting portion 123. A side surface of the rotation structure 110 has a first notch portion 122, the first notch portion 122 being formed as a groove portion extending from the accommodation portion 128 to the exposed portion 129. In the embodiment, the accommodation portion 128 is provided at the proximal side of the rotation structure 110, however, the accommodation portion 128 can be provided at the distal side of the drive shaft 60 instead of at the proximal side of the rotation structure 110.

In an embodiment, the first notch portion 122 is formed in a part of the circumferential direction and is formed in a shape, which is notched in a V shape in a cross-section orthogonal to the axis (see FIG. 3). In the embodiment, the first notch portion 122 is provided at two positions of the circumferential direction, but may be provided only at one position or three or more positions. Further, the first cutting portion 123, which is a blade, is formed by the edge of the first notch portion 122, however, the groove portion and the cutting portion may be provided at different positions of the circumferential direction. In accordance with an exemplary embodiment, when the first cutting portion 123 is formed by the edge of the first notch portion 122 as in the embodiment, the configuration of the first notch portion can be simplified. The first notch portion 122 of the embodiment extends in parallel to the axial direction, but may be inclined with respect to the axial direction as long as the first notch portion extends in the axial direction as a whole instead of that configuration. Further, the first notch portion 122 may extend in a spiral shape.

As illustrated in FIGS. 3 and 4, in the side surface of the accommodation portion 128 of the rotation structure 110, a rolling element holding space 141 in which a rolling element 140 is disposed in a rollable manner is formed at a plurality of positions at intervals in the circumferential direction. In the embodiment, the rolling element holding spaces 141 are equally arranged at two positions with a gap formed between the rolling element holding spaces 141 in the circumferential direction. In accordance with an exemplary embodiment, the first notch portion 122 is disposed between the rolling element holding spaces 141, and wherein the first notch portion 122 is adjacent to the rolling element holding spaces 141 in the circumferential direction. The rolling element 140 contacts the inner peripheral surface of the outer sheath 80 while a part of the rolling element 140 protrudes from the outer peripheral surface of the accommodation portion 128. Accordingly, since a friction resistance when the accommodation portion 128 of the rotation structure 110 rotates with respect to the outer sheath 80 decreases, the rotation structure 110 can rotate relatively smoothly. In accordance with an exemplary embodiment, the rolling element 140 functions as a bearing between the rotation structure 110 and the outer sheath 80 and decreases a friction resistance during the relative rotation of the rotation structure 110 with respect to the outer sheath 80. Accordingly, the generation of friction heat can be reduced.

In accordance with an exemplary embodiment, the first notch portion 122 can be used as a liquid supply channel, which supplies a cooling liquid to the exposed portion 129. In accordance with an exemplary embodiment, a cooling liquid such as a saline solution and contrast medium can be introduced from the proximal side of the outer sheath 80 into the outer sheath 80 and can be supplied to the exposed portion 129 through a space inside the outer sheath 80. A liquid supply catheter may be inserted into the outer sheath 80 and a liquid may be supplied to the first notch portion 122 through the catheter. Further, a syringe or a pump can be used as means for introducing the saline solution into the outer sheath 80, but various liquid supply mechanisms can be employed instead of that configuration.

Further, the first notch portion 122 can constitute a suction channel, which suctions a cut object. In this case, for example, a cut object or the like is suctioned from an opening of the first notch portion 122 formed in the exposed portion 129 through a space inside the outer sheath 80 by a suction force generated by a syringe connected to the proximal side of the outer sheath 80. A configuration may be employed in which a suction catheter is inserted into the outer sheath 80 and a cut object or the like is suctioned through a space inside the suction catheter communicating with the first notch portion 122. In accordance with an exemplary embodiment, a syringe or a pump can be used as means for applying a suction force from the proximal side of the suction catheter or the outer sheath 80, but various suction mechanisms can be employed instead of that configuration.

In accordance with an exemplary embodiment, the rotation structure 110 includes a first annular portion 112, which is provided in the accommodation portion 128 and a second annular portion 111, which is provided in the exposed portion 129. Further, a constricted portion 126 is formed between the first annular portion 112 and the second annular portion 111 in the exposed portion 129 of the rotation structure 110. In the rotation structure 110 of the embodiment, a step portion 115 is provided between the first annular portion 112 and the constricted portion 126 so as to increase in diameter in a step shape at the distal side. The first annular portion 112 may be a proximal end of the first tapered portion 116. The second annular portion 111 may be a distal end of the second tapered portion 114.

In accordance with an exemplary embodiment, the constricted portion 126 includes a first tapered portion 116, which is provided at the distal side of the first annular portion 112 decreasing in diameter toward the distal side and a second tapered portion 114, which is provided at the proximal side of the second annular portion 111 decreasing in diameter toward the proximal side. The first tapered portion 116 of the embodiment decreases in diameter from the step portion 115 toward the distal side. Further, the second tapered portion 114 of the embodiment decreases in diameter from the second annular portion 111 toward the proximal side. The rotation structure 110 of the embodiment has a configuration which includes the above-described step portion 115 and in which the first tapered portion 116 decreases in diameter from the step portion 115 toward the distal side, but may have a configuration which does not include the step portion 115 and in which the first tapered portion 116 decreases in diameter from the first annular portion 112 toward the distal side. Further, in the present disclosure, the second tapered portion 114, the second annular portion 111, and the third tapered portion 113 to be described later are not essential, but the exposed portion 129 may be only the first tapered portion 116.

In accordance with an exemplary embodiment, the constricted portion 126 includes a bottom portion (i.e., lower inner edge) 127, which connects the first tapered portion 116 and the second tapered portion 114 to each other. The diameter of the bottom portion 127 is smaller than the diameter of the first annular portion 112 and the diameter of the second annular portion 111. Here, the "diameter" means a diameter about the rotation axis X of the rotation structure 110. The same description of the diameter of the bottom portion 127 also applies to the description below. The shape of the constricted portion 126 may be formed by the first tapered portion 116 and the second tapered portion 114 having the same maximum diameter. Further, the shape of the constricted portion 126 may be formed by the first tapered portion 116 and the second tapered portion 114 of which the maximum diameter is larger than that of the first tapered portion 116. Further, the shape of the constricted portion 126 may be formed by the first tapered portion 116 of which the maximum diameter is larger than that of the second tapered portion 114 and the second tapered portion 114. The axial length of the constricted portion 126 may be formed by the first tapered portion 116 and the second tapered portion 114 having the same axial length. The axial length of the constricted portion 126 may be formed by the first tapered portion 116 of which the axial length is longer than that of the second tapered portion 114 and the second tapered portion 114. The axial length of the constricted portion 126 may be formed by the first tapered portion 116 and the second tapered portion 114 of which the axial length is longer than that of the first tapered portion 116.

Further, the rotation structure 110 includes the third tapered portion 113, which decreases in diameter from the second annular portion 111 toward the distal side.

In the embodiment, the first notch portion 122 is formed in the first tapered portion 116. In accordance with an exemplary embodiment, the distal side of the first notch portion 122 is terminated before the bottom portion 127, but the first notch portion 122 may be continuous to the second notch portion 120 to be described later instead of that configuration. The first notch portion 122 may be asymmetric or symmetric. In the first notch portion 122, an angle of the surface of the first notch portion 122 opposite to the rotation direction of the rotation structure 110 is larger than that of the surface of the first notch portion 122 in the rotation direction. Further, abrasive grains, grinding stones, or the like may be electrodeposited on the first tapered portion 116. In that case, the first tapered portion 116 with the abrasive grains, grinding stones, or the like becomes a fourth cutting portion. When the first tapered portion 116 includes the first cutting portion 123 of the first notch portion 122 and the fourth cutting portion on which abrasive grains or grinding stones are electrodeposited, the stenotic object can be efficiently cut by the first cutting portion 123 of the first notch portion 122 and the fourth cutting portion on which abrasive grains or grinding stones are electrodeposited. In accordance with an exemplary embodiment, abrasive grains are, for example, diamond abrasive grains or the like.

In accordance with an exemplary embodiment, the second tapered portion 114 includes a second notch portion 120, which is provided in a part of the circumferential direction to be notched in a V shape in a cross-section orthogonal to the axis and a second cutting portion 121 which is a blade is formed by the edge of the second notch portion 120. The second notch portion 120 may be provided only at one position or two or more positions in the circumferential direction. The second notch portion 120 may be asymmetric or symmetric. In the second notch portion 120, an angle of the surface of the second notch portion 120 opposite to the rotation direction of the rotation structure 110 is larger than that of the surface of the second notch portion 120 in the rotation direction. Further, when abrasive grains, grinding stones, or the like are electrodeposited on the second tapered portion 114, the stenotic object can be efficiently cut by the cutting portion on which abrasive grains or grinding stones are electrodeposited and the second cutting portion 121 of the second notch portion 120. Further, the second tapered portion 114 may not include the second notch portion 120, but may include only the cutting portion on which abrasive grains or grinding stones are electrodeposited.

In accordance with an exemplary embodiment, the third tapered portion 113 includes a third notch portion 117, which is formed in a part of the circumferential direction to be notched in a V shape in a cross-section orthogonal to the axis and a third cutting portion 118, which is a blade is formed by the edge of the third notch portion 117. The third notch portion 117 may be provided only at one position or two or more positions in the circumferential direction. The third notch portion 117 may be asymmetric or symmetric. In the third notch portion 117, an angle of the surface of the third notch portion 117 opposite to the rotation direction of the rotation structure 110 is larger than that of the surface of the third notch portion 117 in the rotation direction. Further, when abrasive grains, grinding stones, or the like are electrodeposited on the third tapered portion 113, the stenotic object can be efficiently cut by the cutting portion on which abrasive grains or grinding stones are electrodeposited and the third cutting portion 118 of the third notch portion 117. Further, the third tapered portion 113 may not include the third notch portion 117, but may include only the cutting portion on which abrasive grains or grinding stones are electrodeposited.

Since the first cutting portion 123 and the third cutting portion 118 are formed in a tapered part, which decreases in diameter toward the distal side, the stenotic object S can be effectively cut when pressing (i.e., pushing) the rotation structure 110 toward the distal side. Further, since the second cutting portion 121 is formed in a tapered part, which decreases in diameter toward the proximal side, the stenotic object S can be effectively cut when pulling the rotation structure 110 toward the proximal side. In accordance with an exemplary embodiment, the axial lengths of the first notch portion 122, the second notch portion 120, and the third notch portion 117 are respectively proportional to the axial lengths of the first tapered portion 116, the second tapered portion 114, and the third tapered portion 113.

The second annular portion 111 may be constructed of such a shape and material that an outer peripheral surface of the second annular portion 111 can smoothly come into contact with biological tissues, and the outer peripheral surface may be a first non-cutting portion. Accordingly, with the first non-cutting portion, the risk of damaging the biological tissue can be reduced when cutting the stenotic object S. Further, the third tapered portion 113 may be provided with a second non-cutting portion 119 in which the third notch portion 117 is not formed on the outer peripheral surface of the distal side end portion throughout the entire area in the circumferential portion.

The material, which forms the rotation structure 110 is not particularly limited, for example, the rotation structure 110 material can be stainless steel, Ta, Ti, Pt, Au, W, Ni, NiTi alloy, super steel (WC), high speed (HSS), polyolefins such as polyethylene and polypropylene, polyamides, polyesters such as polyethylene terephthalate, fluorine polymers such as PTFE, polyetheretherketone (PEEK), polyimide, and the like can be appropriately used.

Figure 5A:
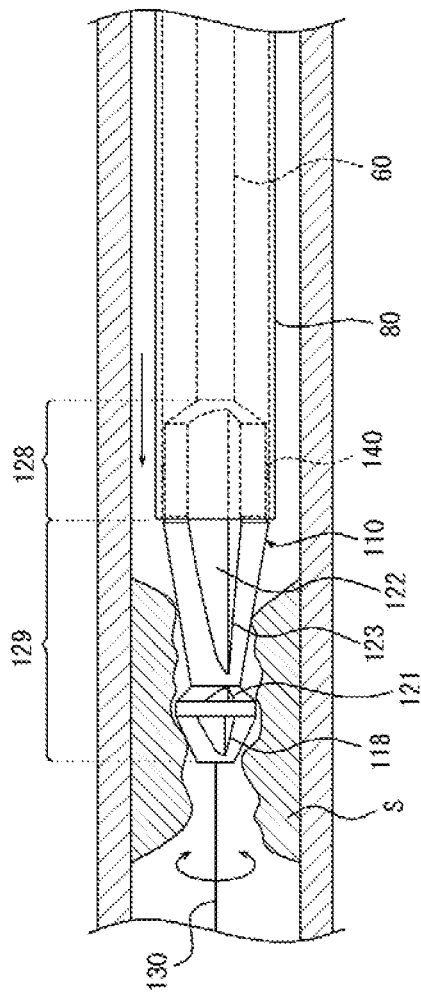
FIGS. 5A and 5B are schematic cross-sectional views illustrating a state inside a blood vessel when performing a procedure using the medical device illustrated in FIG. 1, where
Figure 5B:
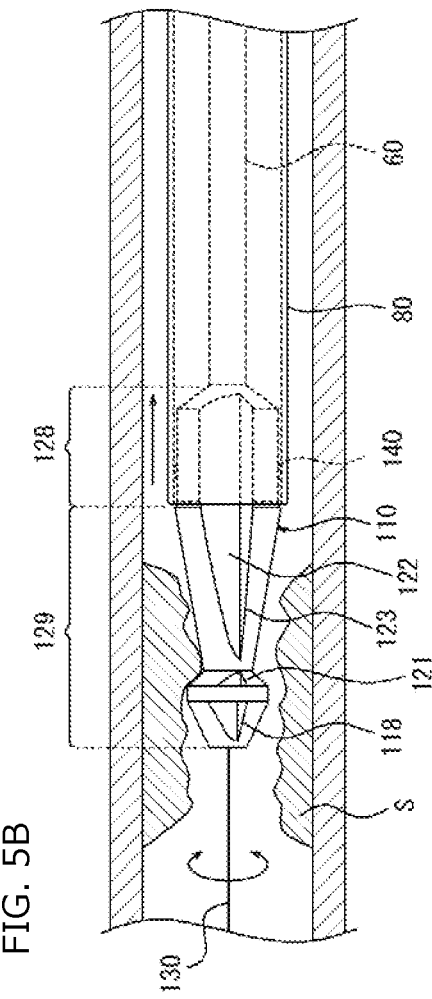

FIGS. 5A and 5B illustrate a state in which a stenotic object S inside a blood vessel is cut by using the medical device 10 according to an exemplary embodiment. FIG. 5A illustrates a state in which the stenotic object S is cut by pressing (i.e., pushing) the rotation structure 110 and FIG. 5B illustrates a state in which the stenotic object S is cut by pulling the rotation structure 110.

As illustrated in FIG. 5A, the rotation structure 110 is first inserted into the blood vessel when pressing the rotation structure 110 and cutting the stenotic object S. Next, when the drive shaft 60 is rotated, the rotation structure 110 rotates and hence the stenotic object S inside the body lumen can be cut by the third cutting portion 118 and the first cutting portion 123. At this time, since the diameter of the bottom portion 127 of the constricted portion 126 is smaller than the diameter of the first annular portion 112 (see FIG. 2) and the diameter of the second annular portion 111 (see FIG. 2), the first cutting portion 123 can be prevented from coming into contact with biological tissues such as normal blood vessels and relatively high safety can be secured.

Further, as illustrated in FIG. 5B, when the drive shaft 60 is rotated when pulling the rotation structure 110 and cutting the stenotic object S, the rotation structure 110 rotates and hence the stenotic object S inside the body lumen can be cut by the second cutting portion 121. At this time, since the diameter of the bottom portion 127 of the constricted portion 126 is smaller than the diameter of the first annular portion 112 and the diameter of the second annular portion 111, the second cutting portion 121 can be prevented from coming into contact with biological tissues such as normal blood vessels and relatively high safety can be secured. Although an unevenness remains on the surface of the stenotic object S due to various factors (factors on whether the stenotic object S is rigid, the rotation of the rotation structure 110 is biased, and the like) just by pressing the rotation structure 110 toward the distal side, the unevenness of the stenotic object S can be reduced by moving the rotation structure 110 toward the proximal side and cutting the stenotic object S by the second cutting portion 121 inside the constricted portion 126.

In the medical device 10 according to the embodiment, the side surface of the rotation structure 110 has the first notch portion 122 formed to extend from the accommodation portion 128 to the exposed portion 129. When the first notch portion 122 is used as a liquid supply channel for supplying a cooling liquid, it is possible to obtain an effect of cooling the rotation structure 110 in such a manner that a cooling liquid is supplied to the vicinity of the cutting portion when the liquid passes through the first notch portion 122 and to help reduce the risk of damaging the biological tissue in accordance with an increase in temperature. Further, since an increase in temperature can be suppressed, it is possible to increase the rotation speed with a larger heat generation amount and to increase the rotation speed of the rotation structure 110. Accordingly, the stenotic object S can be efficiently cut from the inner wall surface of the body lumen. Further, even when the first notch portion 122 is used as a suction channel for suctioning a cut object, it is possible to obtain an effect of cooling the rotation structure 110 in such a manner that a cut object and a liquid inside the body lumen pass through the first notch portion 122 and help reduce the risk of damaging the biological tissue in accordance with an increase in temperature. Further, since an increase in temperature is suppressed, it is possible to increase the rotation speed of the rotation structure 110 and hence to help efficiently cut the stenotic object S from the inner wall surface of the body lumen.

Further, also in the embodiment, the first cutting portion 123 is formed by the edge of the first notch portion 122. Accordingly, when the first notch portion 122 is used as a liquid supply channel, a cooling liquid can be directly supplied to the first cutting portion 123, which is easily heated by friction heat and a cooling effect can be improved. Further, when the first notch portion 122 is used as the suction channel, an object cut can be suctioned by the first cutting portion 123 at a position relatively close to the first cutting portion 123 and suction performance can be improved. Further, since the suction performance is improved, a cooling effect can also be improved. In accordance with an exemplary embodiment, since diamond abrasive grains are electrodeposited on the surface of the first tapered portion 116, the second tapered portion 114, or the third tapered portion 113, a heat generation phenomenon due to the cutting easily occurs when a cutting portion such as grinding stones is provided and hence a cooling effect according to the present disclosure can be more efficiently exhibited.

Further, in the embodiment, the rolling element 140 for serving as a bearing is disposed inside the rotation structure 110, which can make the diameter of the rotation structure 110 smaller than that in a case where a bearing is provided outside the rotation structure 110.

Further, in the embodiment, since the first notch portion 122 is disposed between the rolling element holding spaces 141, and wherein the first notch portion 122 is adjacent to the rolling element holding spaces 141 in the circumferential direction, the rolling element holding space 141 and the first notch portion 122 do not overlap each other in the radial direction and hence the accommodation portion 128 can be decreased in size.

Further, when the first notch portion 122 is used as the suction channel, the first notch portion 122 may desirably extend in a spiral shape from the proximal side toward the distal side to be inclined in the rotation direction of the rotation structure 110. Accordingly, since an object cut by the first cutting portion 123 can be smoothly taken into the first notch portion 122 in accordance with the rotation of the rotation structure 110 when pressing and pulling the rotation structure 110 to cut the stenotic object S, it is possible to improve suction performance.

Further, in the embodiment, the diameter of the second annular portion 111 is smaller than the diameter of the first annular portion 112. Accordingly, when the first notch portion 122 is used as a liquid supply channel, a cooling liquid can be rather easily supplied to a side more distal than the second annular portion 111 and hence a cooling effect can be improved. Further, an object cut at a side more distal than the second annular portion 111 can be rather easily suctioned when the first notch portion 122 is used as the suction channel, which makes it possible to improve suction performance and to improve the cooling effect in accordance with the improvement of the suction performance. Further, since the diameter of the second annular portion 111 is smaller than the diameter of the first annular portion 112, it is possible to smoothly press the rotation structure 110 during the pressing operation.

Further, in the embodiment, the rotation structure 110 further includes the third tapered portion 113, which is provided at a side more distal than the second annular portion 111 to decrease in diameter toward the distal side and the third tapered portion 113 includes the third cutting portion 118. Accordingly, since it is possible to cut the stenotic object S even by the third cutting portion 118 when pressing the rotation structure 110, it is possible to smoothly press the rotation structure 110.

Figure 6:
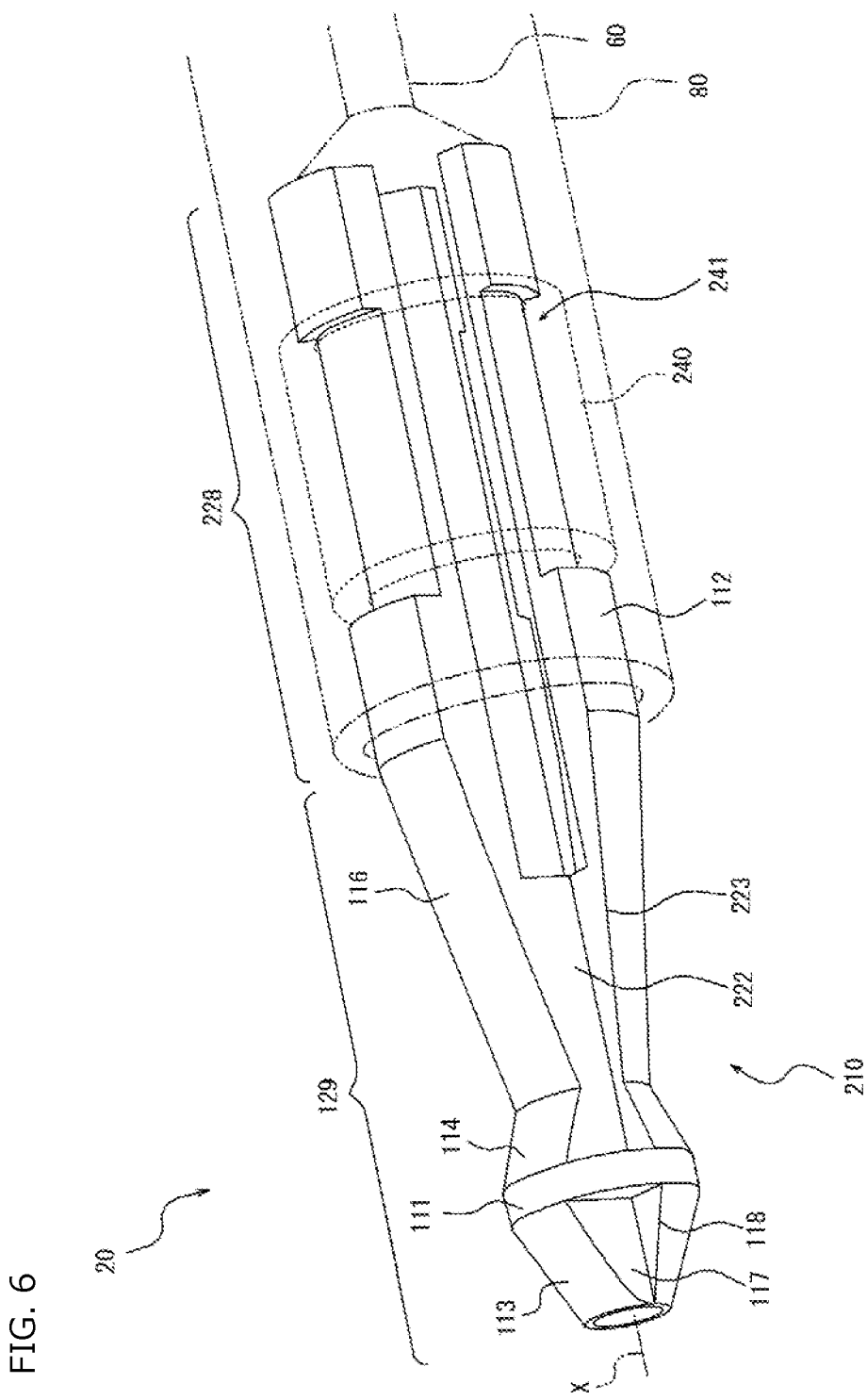
FIG. 6 is an enlarged perspective view of a distal side of a medical device according to another embodiment of the present disclosure.

In accordance with an exemplary embodiment, the bearing which is provided between the outer sheath 80 and the accommodation portion 128 of the rotation structure 110 is not limited to the configuration of the rolling element 140 disposed in the rolling element holding space 141 of the above-described embodiment, but an annular bearing member 240 may be employed, for example, as illustrated in FIG. 6.

In accordance with an exemplary embodiment, a medical device 20 illustrated in FIG. 6 includes an annular bearing member 240 that is provided between the outer sheath 80 and the accommodation portion 228 of the rotation structure 210. The bearing member 240 is disposed in an annular concave portion 241 formed in the accommodation portion 228 of the rotation structure 210 and hence the axial movement of the bearing member 240 with respect to the rotation structure 210 can be regulated.

The bearing member 240 may be fixed to the rotation structure 210. In this case, a sliding movement is allowed at a contact surface with the outer sheath 80 to which the bearing member 240 is not fixed, a friction resistance is relatively small, and a smooth rotation is allowed.

Further, the bearing member 240 may be divided into two parts in the radial direction and the inner annular member and the outer annular member may be relatively rotatable. In that case, a rolling bearing structure including a spherical member or a cylindrical member corresponding to a rolling element may be provided between the inner annular member and the outer annular member and a contact surface between the inner annular member and the outer annular member may be a smoothly slidable surface.

Further, the side surface of the rotation structure 210 has a notch portion 222 formed as a groove portion, and the notch portion 222 is disposed to pass through the inside of the bearing member 240 in the radial direction. In accordance with an exemplary embodiment, the notch portion 222 is continuously formed from the accommodation portion 228 to the first tapered portion 116 and the second tapered portion 114. A cutting portion 223 is formed by the edge of the notch portion 222 of the exposed portion 129.

Modified Example

Figure 7:
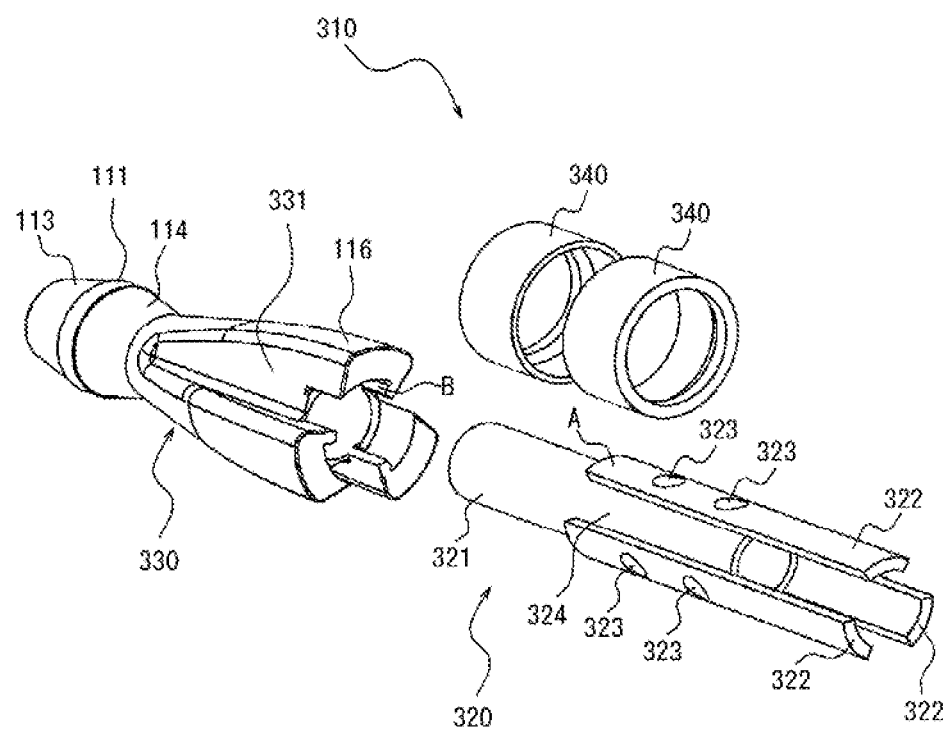
FIG. 7 is an exploded perspective view of a rotation structure according to a modified example.
Figure 8:
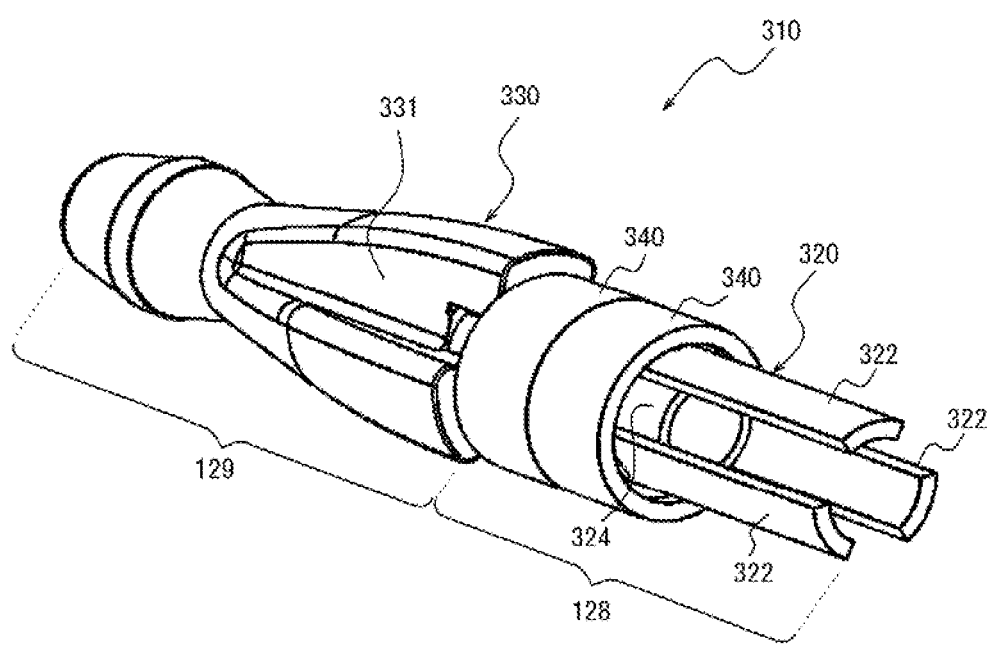
FIG. 8 is a perspective view of a rotation structure according to a modified example.

Referring to FIGS. 7 and 8, a configuration of a rotation structure according to a modified example of the present disclosure will be described. FIG. 7 is an exploded perspective view of a rotation structure 310 according to the modified example. FIG. 8 is a perspective view of the rotation structure 310 according to the modified example.

As illustrated in FIG. 7, the rotation structure 310 is different from the structure illustrated in FIGS. 2 to 6 in that a proximal portion 320 located at the proximal side and a distal portion 330 located at the distal side are separated from each other. The rotation structure 310 includes the proximal portion 320, the distal portion 330, and a ring 340.

In accordance with an exemplary embodiment, the proximal portion 320 includes, as illustrated in FIG. 7, a cylindrical member 321 and three connecting members 322 surrounding the cylindrical member 321.

The connecting member 322 has a hole portion 323. A ball (or balls), for example, for a ball bearing can be received in the hole portion 323 and the ball bearing is formed by the ball and the ring 340.

The side surface of the proximal portion 320 has a concave portion 324 formed as a groove portion. In accordance with an exemplary embodiment, the concave portion 324 is a space, which is formed between the connecting members 322, and wherein the concave portion 324 is adjacent to the connecting members 322 in the circumferential direction and is configured to pass through the inside of the ring 340. In this example, the concave portion 324 is provided at three positions of the circumferential direction. Further, the side surface of the distal portion 330 has a notch portion 331 formed as a groove portion. The notch portion 331 is formed to communicate with the concave portion 324.

FIG. 8 illustrates a case in which the distal portion 330 is set as the exposed portion 129 and an outer sheath (not illustrated) is disposed so that a distal end surface of the outer sheath is in contact with the proximal end surface of the distal portion 330. In accordance with an exemplary embodiment, when the proximal portion 320 and the ring 340 are covered by the outer sheath, the exposed portion 129 and the accommodation portion 128 are formed as illustrated in FIG. 8. The present disclosure is not limited to the exemplary embodiment in which the exposed portion 129 and the accommodation portion 128 as shown in FIG. 8, for example, the distal end surface of the outer sheath may be in contact with the proximal end surface of the ring 340. In this case, the portion more proximal than the ring 340 forms the accommodation portion 128, and the portion more distal than the proximal end surface of the ring 340 forms the exposed portion 129. In accordance with an exemplary embodiment, the groove portion (the concave portion 324 and the notch portion 331) extends from the accommodation portion 128 to the exposed portion 129. In accordance with an exemplary embodiment, the opening of the groove portion (the notch portion 331) of the exposed portion 129 normally communicates with a space inside the outer sheath.

Although not illustrated in FIGS. 7 and 8, the distal end surface of the drive shaft 60 adheres to the proximal end surface of the cylindrical member 321. Further, the outer surface of the drive shaft 60 can adhere to each of the inner surfaces of three connecting members 322.

In accordance with an exemplary embodiment, the cylindrical member 321 may be replaced by the distal portion of the drive shaft 60. For example, the proximal portion 320 may be formed in such a manner that three connecting members 322 adhere to the outer surface of the drive shaft 60. In this case, the distal end surface of the drive shaft 60 may protrude to the side more distal than the distal end surface of the connecting member 322 or reversely the distal end surface of the connecting member 322 may protrude in relation to the distal end surface of the drive shaft 60.

When the drive shaft 60 rotates, the connecting member 322 rotates. Since the distal portion A of the connecting member 322 illustrated in FIG. 7 is fitted to the concave portion B of the distal portion 330, the distal portion 330 rotates when the connecting member 322 rotates.

With such a configuration, the rotation structure 310 is relatively strong against a torque load and a bending load.

The present disclosure is not limited to the above-described embodiment and can be modified into various forms by the person skilled in the art within the technical spirit of the present disclosure. For example, the outer sheath 80 is bendable and, for example, a configuration may be employed in which a predetermined portion at the distal side can be bent by a manual operation or a dedicated operation device at the proximal side and the bent state can be maintained. Further, the body lumen into which the medical device is inserted is not limited to the blood vessel, for example, the body lumen may be a vessel, a ureter, a bile duct, a fallopian tube, a liver tube, or the like.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for cutting an object in a body lumen, comprising:
   a rotatable drive shaft;
   a tubular outer sheath configured to accommodate the drive shaft in a rotatable manner; and
   a rotation structure, the rotation structure comprising:
   one or more rings;
   an accommodation portion configured to be disposed inside the outer sheath;
   an exposed portion, the exposed portion being located at a distal side of the accommodation portion and is provided with a cutting portion, the accommodation portion being configured to be rotatable by the drive shaft;
   a side surface of the accommodation portion and a side surface of the exposed portion have a groove portion, the groove portion extending from the accommodation portion to the exposed portion, and wherein the groove portion is configured to pass through an inside of the one or more rings; and
   the one or more rings being configured to rotate relative to the accommodation portion of the rotation structure.

2. The medical device according to claim 1, wherein the side surface of the accommodation portion has a plurality of rolling element holding spaces formed at intervals in a circumferential direction and each of the plurality of rolling element holding spaces configured to hold a rolling element, and the groove portion is disposed between the plurality of roping element holding spaces.

3. The medical device according to claim 2, wherein the plurality of rolling element holding spaces are equally arranged at two positions with a gap formed between the plurality of rolling element holding spaces in the circumferential direction.

4. The medical device according to claim 2, wherein the groove portion is disposed between the plurality of rolling element holding spaces, which are adjacent to each other in the circumferential direction.

5. The medical device according to claim 2, wherein the rolling element contacts an inner peripheral surface of the outer sheath while a part of the rolling element protrudes from an outer peripheral surface of the accommodation portion.

6. The medical device according to claim 1, wherein an edge of the groove portion forms the cutting portion.

7. The medical device according to claim 1, wherein the groove portion forms a liquid supply channel for supplying a cooling liquid to the exposed portion.

8. The medical device according to claim 1, wherein the groove portion forms a suction channel for suctioning a cut object.

9. The medical device according to claim 1, wherein the exposed portion comprises:
   a proximal portion; a distal portion; and
   a constricted portion provided between the proximal portion and the distal portion, the constricted portion including:
   a first tapered portion having a first cutting portion, the first tapered portion decreasing in diameter toward a distal side of the constricted portion;
   a second tapered portion having a second cutting portion, the second portion decreasing in diameter toward a proximal side of the constricted portion; and
   a bottom portion provided between the first tapered portion and the second tapered portion.

10. The medical device according to claim 9, wherein the bottom portion of the constricted portion has a diameter smaller than a maximum diameter of the proximal portion and a maximum diameter of the distal portion.

11. The medical device according to claim 9, wherein the first tapered portion has a maximum diameter larger than a maximum diameter of the second tapered portion.

12. The medical device according to claim 9, wherein the first cutting portion is a surface of the first tapered portion; the second cutting portion being a surface of the second tapered portion; and
   wherein the distal portion of the exposed portion has a diameter smaller than a diameter of the proximal portion of the exposed portion.

13. The medical device according to claim 9, further comprising:
   a third tapered portion which is provided on a side more distal than a distal portion of the constricted portion, the third tapered portion decreasing in diameter toward the distal portion of the exposed portion, and wherein the third tapered portion includes a third cutting portion.

14. The medical device according to claim 1, wherein the groove portion in the accommodation portion is a concave portion formed from a cylindrical member and one or more connecting members surrounding the cylindrical member.

15. The medical device according to claim 1, wherein the accommodation portion of the rotation structure includes one or more connecting members, the one or more connecting members including one or more hole portions, each of the one or more hole portions configured to receive a ball, and wherein the one or more hole portions and the one or more rings form a ball bearing with the ball in each of the one or more hole portions.

16. A method for cutting substances inside a body lumen using a medical device including a rotatable drive shaft, a tubular outer sheath configured to accommodate the drive shaft in a rotatable manner, and a rotatable rotation structure, the rotation structure comprising one or more rings, an accommodation portion configured to be disposed inside the outer sheath, an exposed portion, the exposed portion being located at a distal side of the accommodation portion and is provided with a cutting portion, the accommodation portion being configured to be rotatable by the drive shaft, and a side surface of the accommodation portion and a side surface of the exposed portion have a groove portion, the groove portion extending from the accommodation portion to the exposed portion, and wherein the groove portion is configured to pass through an inside of the one or more rings, the one or more rings being configured to rotate relative to the accommodation portion of the rotation structure, the method comprising:

inserting the rotatable rotation structure into the body lumen;

moving the rotatable rotation structure in a distal direction;

rotating the rotatable rotation structure with the rotatable drive shaft; and cutting the substances inside the body lumen with the rotatable rotation structure during the movement of the rotatable rotation structure in the distal direction.

17. The method according to claim 16, further comprising:

moving the rotatable rotation structure in a proximal direction; and cutting the substances inside the body lumen with the rotatable rotation structure during the movement of the rotatable rotation structure in the proximal direction.

18. The method according to claim 16, further comprising:

injection a cooling liquid to the exposed portion through the groove portion of rotatable rotation structure.

19. The method according to claim 16, further comprising:

introducing a contrast medium from a proximal side of the outer sheath into the outer sheath; and supplying the contrast medium to the exposed portion of the rotatable rotation structure through a space inside the outer sheath and the groove portion of rotatable rotation structure.

20. The method according to claim 16, further comprising:

suctioning the cut substances from the inside of the body lumen through the groove portion of the rotatable rotation structure.

21. The method according to claim 16, wherein the accommodation portion of the rotation structure includes one or more connecting members, the one or more connecting members including one or more hole portions, each of the one or more hole portions configured to receive a ball, and wherein the one or more hole portions and the one or more rings form a ball bearing with the ball in each of the one or more hole portions.

* * * * *